United States Patent [19]

Chandran et al.

[11] Patent Number: 5,609,857

[45] Date of Patent: *Mar. 11, 1997

[54] METHODS OF CONDITIONING HAIR WHICH UTILIZE POLYMERIC N-VINYL FORMAMIDE

[75] Inventors: Rama S. Chandran, S. Bound Brook; Jean-Pierre Leblanc, Somerville; John C. Leighton, Flanders; Gary T. Martino, Plainsboro, all of N.J.

[73] Assignee: National Starch and Chemical Investment Holding Corporation, Wilmington, Del.

[*] Notice: The term of this patent shall not extend beyond the expiration date of Pat. No. 5,478,553.

[21] Appl. No.: 417,369

[22] Filed: Apr. 5, 1995

[51] Int. Cl.$^6$ ................................................ A61K 7/075
[52] U.S. Cl. .................. 424/70.1; 424/70.11; 424/70.16
[58] Field of Search ............................. 424/70.1, 70.11, 424/70.16

[56] References Cited

U.S. PATENT DOCUMENTS

| | | | |
|---|---|---|---|
| Re. 34,713 | 8/1994 | Itagaki et al. | 525/328.4 |
| 2,628,224 | 1/1951 | Le Sueur Cairns et al. | 260/89.7 |
| 3,212,972 | 10/1965 | Bailey, Jr. | 167/87.1 |
| 4,240,450 | 12/1980 | Grollier et al. | 132/7 |
| 4,402,977 | 9/1983 | Grollier et al. | 424/70 |
| 4,421,602 | 12/1983 | Brunnmueller et al. | 162/168.2 |
| 4,578,515 | 3/1986 | Dawson et al. | 564/215 |
| 4,623,699 | 11/1986 | Brunnmueller et al. | 525/355 |
| 4,713,236 | 12/1987 | Hoover et al. | 424/70 |
| 4,906,777 | 3/1990 | Pinschmidt, Jr. et al. | 564/215 |
| 4,942,259 | 7/1990 | Parris et al. | 564/187 |
| 5,021,238 | 6/1991 | Martino et al. | 424/47 |
| 5,037,927 | 8/1991 | Itagaki et al. | 526/307.7 |
| 5,037,930 | 8/1991 | Shih | 527/301 |
| 5,064,909 | 11/1991 | Itagaki et al. | 525/340 |
| 5,262,008 | 11/1993 | Moench et al. | 162/168.2 |
| 5,270,379 | 12/1993 | McAndrew et al. | 524/555 |
| 5,373,076 | 12/1994 | Pinschmide, Jr. et al. | 526/303.1 |
| 5,387,641 | 2/1995 | Yeung et al. | 524/557 |
| 5,478,553 | 12/1995 | Chandran et al. | 424/70.17 |

FOREIGN PATENT DOCUMENTS 2040601  4/1991  Canada.

OTHER PUBLICATIONS

Vinamer™EF—Experimental Monomer for Amide–and Amine–Functional Polymer Systems, Information Bulletin.

*Primary Examiner*—Amy Hulina
*Attorney, Agent, or Firm*—William K. Wissing

[57] ABSTRACT

The present invention relates to hair conditioning compositions which utilize as a hair conditioning additive a water-soluble polymer in amounts effective to impart hair conditioning properties to the hair conditioning composition, wherein the polymer contains the residue of N-vinyl formamide and the residue of at least one vinyl polymerizable moiety which contains an amine selected from the group consisting of secondary, tertiary and quaternary amines. The conditioning composition also includes one or more ingredients such as conditioning agents, emulsifiers, viscosity modifiers, gelling agents, opacifiers, stabilizers, preservatives, sequestering agents, chellating agents, pearling agents, clarifying agents, fragrances, colorants, and propellants; and water. The invention also relates to methods of conditioning hair.

10 Claims, No Drawings

METHODS OF CONDITIONING HAIR WHICH UTILIZE POLYMERIC N-VINYL FORMAMIDE

FIELD OF THE INVENTION

This invention relates to hair conditioning compositions which utilize as a hair conditioning additive polymers containing the residue of vinyl polymerizable moieties which contain a secondary, tertiary or quaternary amine and to methods of conditioning hair.

BACKGROUND OF THE INVENTION

Hair conditioning agents are functional additives used in hair care products such as lotions, shampoos, creme rinses, mousses and setting gels to improve the tactile and physical properties of hair. Such properties include, for example, substantivity of the conditioning agent on the hair without excessive build-up and enhancement of hair manageability, i.e., wet combability, dry combability, neutralization of static charge generated by combing and ease of styling. Other properties include lubrication of the hair to reduce friction between hair and comb and to minimize tangling. The additive should also soften the hair and impart gloss to dull hair and smooth the feel of the hair by filling in gaps or flattening cuticle scales. It is also advantageous for the hair conditioner to improve set retention of the hair.

Cationic quaternary ammonium compounds, both mono- and di-functional, low molecular weight quaternary ammonium salts and certain high molecular weight polymers, are employed as conditioning additives in hair care products such as shampoos, conditioners, creme rinses, mousses, sprays and setting gels to impart wet and dry combability, improve feel, enhance curl retention and impart antistatic properties to hair. The Cosmetics, Toiletries and Fragrances Association (CTFA) has established a designation index for compounds employed in cosmetic and toiletry products. Two low molecular weight quaternary ammonium compounds that are commonly used in haircare products because of their low cost are stearylbenzyldimethylammonium chloride (CTFA designation—stearalkonium chloride) and cetyltrimethylammonium chloride (CTFA designation—cetrimonium chloride).

The high molecular weight, cationic quaternary ammonium polymers (polyquats) are being used increasingly in hair care products because of their reported advantages over the simple quaternary ammonium salts in enhancing wet combability, mending split ends and improving appearance. Commonly used polyquats include: UCARE™ Polymer JR (CTFA designation—Polyquaternium 10) from Union Carbide, a quaternized cellulose; Gafquat™ (CTFA designation—Polyquaternium 11) from International Specialty Products, a quaternized copolymer of vinylpyrrolidone and dimethylaminoethylmethacrylate; and Merquat™550 (Polyquaternium 7) from Calgon, a homopolymer of dimethyldiallylammonium chloride.

These quaternary ammonium conditioning additives have in common the quaternary ammonium functional group:

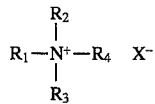

where $R_1$ through $R_4$ may be various substituted or unsubstituted alkyl or aryl substituents, or in the case of the polyquats, represent alkylene or arylene segments of a polymer chain. Associated with the positively charged quaternary ammonium nitrogen atom is a negatively charged counterion. This anion, $X^-$ may be a halide, hydroxide, methylsulfate or similar negatively charged group.

While it is known that copolymers of vinylpyrrolidone and quaternary ammonium compounds are used as hair conditioning additives in hair conditioning compositions, it is desirable to develop new polymers which can be used as a hair conditioning additive.

SUMMARY OF THE INVENTION

The present invention relates to hair conditioning compositions which utilize as a hair conditioning additive a water-soluble polymer in amounts effective to impart hair conditioning properties to the hair conditioning composition, wherein the polymer comprises the residue of N-vinyl formamide and the residue of at least one vinyl polymerizable moiety which contains an amine selected from the group consisting of secondary, tertiary and quaternary amines. The conditioning composition also includes one or more ingredients selected from the group consisting of conditioning agents, emulsifiers, viscosity modifiers, gelling agents, opacifiers, stabilizers, preservatives, sequestering agents, chelating agents, pearling agents, clarifying agents, fragrances, colorants, and propellants; and water. The hair conditioning polymers may further include the residue of at least one vinyl monomer, as that term is defined herein. The invention is also directed to methods of conditioning hair which comprise applying to the hair an amount of the conditioning composition of the present invention which is effective to condition the hair.

DETAILED DESCRIPTION OF THE INVENTION

N-vinyl formamide (NVF) is available from Air Products and Chemicals, Inc., Allentown, Pa., under the trade name Vinamer™ EF. Processes for preparing N-vinyl formamide are disclosed in U.S. Pat. No. 4,578,515, 4,906,777, 4,942,259 and 5,037,927. In the present invention, NVF is not hydrolyzed prior to preparation of the hair conditioning polymer.

The vinyl polymerizable moiety contains at least one amine group selected from the group consisting of secondary, tertiary and quaternary amines. The term "vinyl polymerizable moiety", as used herein, is meant to include those moieties that will copolymerize with NVF, other than "vinyl monomers", as that term is defined herein. Particularly preferred vinyl polymerizable moieties are the quaternary amine-containing moieties. Suitable moieties containing a quaternary amine include, for example, methacrylatoethyltrimethyl ammonium sulfate (MAETAS), methacrylamidopropyltrimethyl ammonium chloride (MAPTAC) and dimethyl diallyl ammonium chloride (DMDAAC). Preferred quaternary amine-containing moieties are MAPTAC and DMDAAC.

The secondary and tertiary amines may be nonionic or cationic, although cationic amines are preferred. In certain embodiments, nonionic secondary and tertiary amines, such as t-butyl aminoethyl methacrylate (t-BAEM), dimethylaminoethyl methacrylate (DMAEMA) and dimethylaminopropyl methacrylamide (DMAPMA) are converted to cationic amines. One method for such conversion is to neutralize the secondary or tertiary amines with an appropriate acid to form an ammonium salt. Alternatively, the secondary or tertiary amines may be reacted with quaternizing agents to form quaternary amines. Such quaternizing agents include, for example, alkyl halides such as methyl chloride, or dialkyl sulfates such as dimethyl sulfate. One skilled in the art will recognize that there may be other routes to convert the nonionic secondary and tertiary amines to cationic amines. Suitable moieties containing a nonionic tertiary amine include, for example, DMAEMA and DMAPMA. Suitable moieties containing a nonionic secondary amine include, for example, t-BAEM.

In certain embodiments, the polymer may be a copolymer comprising the residue of N-vinyl formamide and the residue of the vinyl polymerizable moiety. Preferably, the copolymer comprises from about 50 to about 95 weight percent of the residue of NVF and from about 5 to about 50 weight percent of the residue of the vinyl polymerizable moiety. More preferably, the copolymer comprises from about 60 to about 90 weight percent of the residue of NVF and from about 30 to about 10 weight percent of the residue of the vinyl polymerizable moiety. Most preferably, the copolymer comprises from about 75 to about 85 weight percent of the residue of NVF and from about 25 to about 15 weight percent of the residue of the vinyl polymerizable moiety.

In other embodiments, the polymer may further comprise the residue of at least one vinyl monomer(s). The term "vinyl monomer", as used herein, refers to vinyl monomers which are copolymerizable with NVF and which do not contain secondary, tertiary or quaternary amines. Suitable vinyl monomers include, (a) styrene and derivatives thereof, (b) $C_1$–$C_{18}$ alkyl esters of acrylic acid, (c) $C_1$–$C_{18}$ alkyl esters of methacrylic acid, (d) vinyl esters of the formula $CH_2$=CH-OCOR where R is $C_1$–$C_{18}$, (e) alkyl substituted acrylamides and methacrylamides of the formula $CH_2$=CR-$CONR_1R_2$ where R is H or $CH_3$; $R_1$ is H or $C_1$–$C_{12}$ and $R_2$ is $C_1$–$C_{18}$, (f) monoesters and diesters of fumaric, itaconic and maleic acids, (g) vinyl ethers such as methyl vinyl ether, isobutyl vinyl ether and the like, (h) hydroxy functional acrylates and methacrylates such as hydroxyethyl acrylate, hydroxypropyl acrylate, hydroxyethyl methacrylate and hydroxypropyl methacrylate, (i) acrylamide, (j) non-alkyl substituted acrylamides such as diacetone acrylamide, and (k)cyclic amides such as vinylpyrrolidone and vinylcaprolactam.

The hair conditioning compositions of the present invention comprise an amount of the hair conditioning polymer which is effective to impart hair conditioning properties to the hair conditioning compositions. Typically, the hair conditioning compositions comprise from about 0.1 to about 15 weight percent of the polymer, preferably from about 0.25 to about 10 weight percent of the polymer, based on the total weight of the hair conditioning composition.

In one embodiment, the hair conditioning composition is a conditioning lotion. In addition to the inventive conditioning polymer, the lotion may further comprise other conditioning agents, such as cationic surfactants, fatty acid salts, hydrolyzed proteins such as collagen, keratin and amino acids, and oily materials such as lanolin, fatty alcohols, waxes and botanical oils. The lotion may also further comprise other ingredients such as emulsifiers, viscosity modifiers, opacifiers, pearlizers, stabilizers, preservatives, fragrances and colorants. In certain embodiments, the lotion may be applied via a spray delivery system.

In other embodiments, the hair conditioning composition is a conditioning shampoo. The shampoos generally comprise primary surfactants for cleansing and foam, secondary surfactants for cleansing, foam boosting and conditioning and additional additives for special performance, stability, fragrance and color. More specifically, these aqueous-based systems may contain surfactants, conditioning agents such as cationic or amphoteric surfactants, oily materials, proteins, botanicals, synthetic resins and silicone polymers, in addition to other additives such as sequestering or chelating agents, viscosity modifiers, opacifying, pearling or clarifying agents, stabilizers, fragrances, colorants and preservatives.

The hair conditioning composition also may comprise a gelling agent in amounts effective to form a conditioning gel. Preferably, the conditioning gel comprises from about 0.05 to about 3 weight percent of the gelling agent, more preferably from about 0.1 to about 1.0 weight percent of the gelling agent, based on the total weight of the conditioning gel. Examples of such gelling agents include synthetic polymers such as the acrylic-based Carbopol® series of thickeners available from B. F. Goodrich, Cleveland, Ohio and associative thickeners such as Aculyn™, available from Rohm & Haas, Philadelphia, Pa. Other exemplary gelling agents include, cellulosic thickeners, such as derivatized hydroxyethyl cellulose and methyl cellulose, starch-based thickeners, such as acetylated starch, and naturally occurring gums, such as agar, algin, gum arabic, guar gum and xanthan gum.

In yet other embodiments, the hair conditioning composition may be in the form of mousse or spray. The mousse or spray may contain, in addition to the ingredients mentioned herein above, propellants such as ethers, compressed gases, halogenated hydrocarbons and hydrocarbons. Exemplary propellants are dimethyl ether, propane, butane, 1,1-difluoroethane, and mixtures thereof.

The hair conditioning compositions may include organic solvents to modify certain properties of the hair conditioning compositions, such as viscosity, solubility or drying. Typical solvents include, for example, ethanol, isopropanol, acetone, dimethoxymethane and methyl ethyl ketone. When used, the amounts of organic solvents preferably are minimized. More preferably, the compositions will be free of organic solvents.

The hair conditioning compositions will contain from about 0.5 to about 20 weight percent of one or more ingredients selected from the group consisting of conditioning agents, emulsifiers, viscosity modifiers, gelling agents, opacifiers, stabilizers, preservatives, sequestering agents, chelating agents, pearling agents, clarifying agents, fragrances, colorants, and propellants. Preferably, the composition will comprise from about 1 to about 10 weight percent of the one or more ingredients.

The invention is also directed to methods of conditioning hair which comprise applying to the hair an amount of the conditioning composition of the present invention which is effective to condition the hair. By conditioning the hair, it is meant that the hair conditioning composition will impart at least one conditioning property to the hair, or improve at least one hair conditioning property of the hair, as those properties are discussed herein.

The following examples are indicative of preferred hair conditioning compositions and hair conditioning polymers utilized therein. They are not intended and should not be construed to limit the scope of the claims appended hereto. All percentages noted herein are weight percent unless noted otherwise.

Polymer Preparation by Solution Polymerization

The polymers were prepared in 4-neck, 2-L flasks equipped with a stirring shaft powered by a mechanical stirrer, 2 addition funnels, water bath, thermometer and reflux condenser. In the flask were introduced the initial charge of 18 g of NVF, 4.5 g of a 53.0% aqueous solution of MAPTAC, 53.5 g of a 70:30 ethanol/water mixture (wt %), 10 g of water, and 1.12 g of t-butyl peroctoate. The mixture was brought to reflux to allow formation of a solvent atmosphere blanket about the reagents. After 15 min of reflux, a monomer slow-add of the following composition was regularly and continuously added over a period of 4 hours, the refluxing conditions being maintained: 142 g NVF, 35.5 g of a 53.0% aqueous solution of MAPTAC and 235 g of water. Two hours after the beginning of the above addition, a mixture of 26.5 g of a 70:30 ethanol/water mixture (wt%) and 0.2 g of t-butyl peroctoate was regularly and continuously added over a period of 2 hours. When the above slow-adds had been introduced a post-scavenging slow-add composed of 37 g of a 70:30 EtOH/water mixture (wt%) and 0.66 g of t-butyl peroctoate was added regularly and continuously over a period of 3 hours, refluxing conditions being maintained. This was followed by a hold period of 5 hours during which reflux was also maintained. After cooling, the setup was modified by the incorporation of a Dean-Stark trap. The organic solvent was distilled off, steam being introduced above the reaction mixture when the vapor temperature had reached 90° C. When the reflux temperature had reached 100° C., steam was injected subsurface and the operation maintained for 15 min.

The final aqueous solution appeared clear and was diluted to 19.4% solids content. The polymer was designated Polymer B (NVF 88/MAPTAC 12). The final polymer had a inherent viscosity of 1.27 dl/g$^{-1}$. Inherent viscosity (I.V.) was determined on 1 wt % polymer in 1N KCl aqueous solutions. GPC analysis was performed at 80° C. in 0.03N NaNO$_3$ DMSO solutions. Dextrans were used as standards. GPC analysis gave the following data:

$$Mn=6.3\times10^4; Mw=3.9\times10^5; Ip \text{ (polydispersity, i.e., } Mw/Mn)=6.3.$$

The following copolymers were prepared using the above procedure, the amount of monomer used being calculated to meet the formulated final composition:

Polymer A: NVF 80/MAPTAC 20
Polymer C: NVF 80/DMDAAC 20

Procedures for Evaluation of Conditioning Compositions

Polymers A–C were evaluated against a control as a hair-conditioning additive with respect to the following properties: wet combability, dry combability, gloss, presence of static flyaway, flakiness and feel. Details of the test are described below.

The polymers were evaluated as 2% active aqueous solutions and compared to a control consisting of water. Virgin dark brown hair was obtained from DeMeo Brothers, 129 W. 28th Street, New York, N.Y. 10001. A separate 5.25 gram hair swatch, 10" in length, was used for each polymer or water treatment.

Swatches were saturated with tepid water. Excess water was removed by squeezing the wet swatch between the thumb and index finger. Five drops of the test solution were dropped along the length of the swatch and were worked into the swatch using 10 (ten) downward strokes. The swatch samples were grouped as pairs (polymer-treated versus water-treated). A total of eight pairs of samples were evaluated. Performance was evaluated by a trained panel of four members, who compared the coded, inventive polymers to a control of only water. Each member on the panel rated two pairs of samples (polymer vs. water) as being inferior/ superior (−/+) one to the other, or as no statistical difference (NS). Eight pairs in all were tested for each polymer. Each swatch was evaluated as follows:

1. Wet combability—The swatch was gently combed several times and rated for ease of comb-out.

After drying for one hour at 120° F., the following properties were evaluated:

2. Gloss—The swatch was visually rated for gloss and sheen.
3. Stiffness—The swatch was handled by the panelist and rated for stiffness versus softness according to the resistance felt when attempting to bend the hair swatch.
4. Dry Combability—The swatch was gently combed several times and rated for ease of comb-out.
5. Flakiness—The swatch was visually examined for flaking following combing.
6. Static flyaway—The swatch was vigorously combed and then rated for the extent of static flyaway exhibited.
7. Feel—The swatch was evaluated for tactile properties by the panelist.

Data acquired from these methods are qualitative and not quantitative, and therefore subjective. However, panelists who participated in these blind studies have been trained in the analysis of hair swatches for these properties. Additionally, the subjective evaluations are statistically analyzed to identify differences at the 90% confidence level. Results of the evaluation are found in Table 1.

TABLE 1

| Property | Polymer A | Polymer B | Polymer C |
| --- | --- | --- | --- |
| Wet Combability | + | NS | + |
| Gloss | + | + | NS |
| Stiffness | + | + | + |
| Dry Combability | − | − | − |
| Flakiness | − | − | − |
| Static Flyaway | − | − | NS |
| Feel | NS | NS | NS |

As the results indicate, NVF/MAPTAC Polymers A and B exhibit hair conditioning properties, such as improved hair gloss and stiffness, while Polymer A exhibited improved wet combability. Additionally, although not statistically different (NS) under the test criteria, a majority of the samples utilizing Polymer B were found to improve wet combability. The NVF/DMDAAC Polymer C was found to improve wet combability and stiffness. Additionally, although not statistically different under the test criteria, a majority of the panelists found Polymer C to improve static flyaway and the feel of the hair. As indicated herein, additional vinyl monomers may be used in combination with the NVF monomer and the vinyl polymerizable moiety to modify or improve certain hair conditioning properties of the of the conditioning compositions.

The following are hair conditioning formulations in which the inventive hair conditioning polymers may be used. As one skilled in the art will recognize, once armed with the present specification, the formulations are not inclusive of all conditioning formulations anticipated by the present invention. Additionally, each class of conditioner represented by the formulations may include other ingredients such as those discussed herein above. Parts by weight of the conditioning polymer are on a dry weight basis.

Hair Conditioning Formulations

| Conditioning Lotion: | |
| --- | --- |
| Ingredient | Parts by weight |
| Conditioning Polymer | 1.00 |
| Carbopol® 940 thickener | 0.15 |
| Triethanolamine | 0.15 |
| Deionized Water | 98.70 |
| | 100.00 |

Procedure: The Carbopol® 940 thickener is dispersed in water with good agitation. The conditioning polymer is added to the water and mixed until dissolved. While mixing, triethanolamine is added. Mixing is continued until a homogeneous mixture is produced.

| Conditioning Shampoo | |
| --- | --- |
| Ingredient | Parts by weight |
| Conditioning Polymer | 1.80 |
| TEA Lauryl Sulfate | 25.00 |
| Cocamide DEA | 5.00 |
| Dowicil® 200 preservative | 0.10 |
| Deionized Water | 68.10 |
| | 100.00 |

Procedure: The conditioning polymer is dissolved in 20 parts water. In a separate container, the remaining water is heated to 70° C. TEA Lauryl Sulfate and Cocamide DEA are then added to the heated water. The polymer solution from step 1 is added to the heated water. The mixture is cooled to 40° C. and the preservative is added. The mixture is cooled to room temperature. Dowicil® 200 is available from The Dow Chemical Company, Midland, Mich.

| Conditioning Gel | |
| --- | --- |
| Ingredient | Parts by weight |
| Conditioning Polymer | 3.00 |
| Triethanolamine (TEA) | 0.60 |
| Deionized Water | 47.85 |
| Carbopol® 940 thickener | 0.60 |
| Dowicil® 200 preservative | 0.10 |
| Deionized Water | 47.85 |
| | 100.00 |

The polymer and TEA are mixed in D.I. water until homogenous. In a separate vessel, the Dowicil® 200 preservative and Carbopol® 940 thickener are combined with D.I. water and mixed until the thickener goes into solution. Parts A and B are then combined and mixed gently until a clear viscous gel is formed.

| Conditioning Mousse | |
| --- | --- |
| Ingredient | Parts by Weight |
| Conditioning Polymer | 2.50 |
| Tergitol® NP15 surfactant | 0.50 |
| Brij® 97 surfactant | 0.30 |
| Dowicil® 200 preservative | 0.10 |
| Propellant (20:80/Propane:butane) | 10.00 |
| Water | 86.60 |
| | 100.00 |

Procedure: The conditioning polymer is dissolved in water with adequate agitation. The surfactants and preservative are added and the solution is mixed until homogenous. The product is filtered and filled into a container. The container is then charged with the propellant. Tergitol® NP15 surfactant is available from Union Carbide Chemical and Plastics Company, Danbury, Connecticut. Brij® 97 surfactant is available from ICI Specialty Chemicals, Wilmington, Del.

In addition to the subjective, stiffness evaluation performed by the trained panel, Polymer A was formulated into the above conditioning mousse formulation and compared to three comparative polymers, each of which also was formulated into the above mousse formulation. Comparative Polymers D and E are quaternary ammonium polymers formed by the reaction of diethyl sulfate and a copolymer of vinyl pyrrolidone and dimethyl aminoethylmethacrylate. Comparative Polymer F is a polyvinylpyrrolidone homopolymer. Each of the formulated mousses were tested on three dampened 4.5 inch Brown Virgin Italian hair swatches. To each swatch was applied 0.2 g of the respective mousse. The mousse was worked into the swatch and each swatch dried in an oven at 110° F. for two hours. The swatches were placed in a constant temperature and humidity chamber at 50% relative humidity and 23° C. and allowed to remain therein overnight. The stiffness of the swatches were measured using an appropriate device for measuring stiffness. The results were statistically analyzed and reported at the 95% confidence level. The mousse formulated with Polymer A had a stiffness value 24% greater than that of a mousse formulated with Comparative Polymers D and F and 32% greater than a mousse formulated with Comparative Polymer E. The improved stiffness is particularly important to conditioning gel, mousse and spray embodiments of the present invention.

We claim:

1. A method for conditioning hair, the method comprising:

applying to the hair an amount of a hair conditioning composition which is effective to condition the hair, wherein the hair conditioning composition comprises:

a hair conditioning polymer in amounts effective to impart hair conditioning properties to the hair conditioning composition, wherein said polymer is prepared by polymerizing N-vinyl formamide monomer and at least one vinyl polymerizable moiety which contains an amine selected from the group consisting of secondary, tertiary and quaternary amines, one or more ingredients selected from the group consisting of conditioning agents, emulsifiers, viscosity modifiers, gelling agents, opacifiers, stabilizers, preservatives, sequestering agents, chelating agents, pearling agents, clarifying agents, fragrances, colorants, and propellants; and water.

2. The method of claim 1 wherein the hair conditioning polymer is prepared from about 50 to 95 weight percent of the vinyl polymerizable moiety, based on the total weight of the N-vinyl formamide monomer and the vinyl polymerizable moiety.

3. The method of claim 2 wherein the vinyl polymerizable moiety is selected from the group consisting of methacrylatoethyltrimethyl ammonium sulfate methacrylamidopropyltrimethyl ammonium chloride, dimethyl diallyl ammonium chloride, dimethylaminoethyl methacrylate, dimethylaminopropyl methacrylamide and t-butyl aminoethyl methacrylate.

4. The method of claim 1 wherein the hair conditioning polymer is prepared from about 50 to 95 weight percent of the N-vinyl formamide monomer, about 50 to about 5 weight percent of the vinyl polymerizable moiety at least one vinyl monomer(s), based on the total weight of the N-vinyl formamide monomer, the vinyl polymerizable moiety and the vinyl monomer.

5. The method of claim 4 wherein the vinyl monomer(s) is selected from the group consisting of (a) styrene, (b) $C_1$–$C_{18}$ alkyl esters of acrylic acid, (c) $C_1$–$C_{18}$ alkyl esters of methacrylic acid, (d) vinyl esters of the formula $CH_2$=Ch—OCOR where R is $C_1$–$C_{18}$, (e) alkyl substituted acrylamides and methacrylamides of the formula $CH_2$=CR—CONR$_1$R$_2$ where R is H or $CH_3$; $R_1$ is H or $C_1$–$C_{12}$ and $R_2$ is $C_1$–$C_{18}$, (f) monoesters and diesters of fumaric, itaconic and maleic acids, (g) vinyl ethers, (h) hydroxy functional acrylates and methacrylates, (i) acrylamide, (j) diacetone acrylamide, and (k) cyclic amides.

6. The method of claim 1 wherein the hair conditioning composition comprises from about 0.05 to about 15 weight percent of the hair conditioning polymer, based on the total weight of the hair conditioning composition.

7. The method of claim 2 wherein the hair conditioning composition comprises from about 0.05 to about 15 weight percent of the hair conditioning polymer, based on the total weight of the hair conditioning composition.

8. The method of claim 1 wherein the hair conditioning composition is selected from the group consisting of conditioning lotions, shampoos, sprays, mousses and gels.

9. A method for conditioning hair, the method comprising:

applying to the hair an amount of a hair conditioning composition which is effective to condition the hair, wherein the hair conditioning composition comprises:

from about 0.05 to about 15 weight percent of a hair conditioning polymer, based on the total weight of the hair conditioning composition, wherein said polymer is prepared by polymerizing N-vinyl formamide monomer and at least one vinyl polymerizable moiety which contains an amine selected from the group consisting of secondary, tertiary and quaternary amines, one or more ingredients selected from the group consisting of conditioning agents, emulsifiers, viscosity modifiers, gelling agents, opacifiers, stabilizers, preservatives, sequestering agents, chelating agents, pearling agents, clarifying agents, fragrances, colorants, and propellants; and water.

10. A method for conditioning hair, the method comprising:

applying to the hair an amount of a hair conditioning composition which is effective to condition the hair, wherein the hair conditioning composition comprises:

a hair conditioning polymer in amounts effective to impart hair conditioning properties to the hair conditioning composition, wherein said polymer is prepared by polymerizing N-vinyl formamide monomer and at least one vinyl polymerizable moiety which contains an amine selected from the group consisting of methacrylatoethyltrimethyl ammonium sulfate, methacrylamidopropyltrimethyl ammonium chloride, dimethyl diallyl ammonium chloride, dimethylaminoethyl methacrylate, dimethylaminopropyl methacrylamide and t-butyl aminoethyl methacrylate, one or more ingredients selected from the group consisting of conditioning agents, emulsifiers, viscosity modifiers, gelling agents, opacifiers, stabilizers, preservatives, sequestering agents, chelating agents, pearling agents, clarifying agents, fragrances, colorants, and propellants; and water.

* * * * *

UNITED STATES PATENT AND TRADEMARK OFFICE
CERTIFICATE OF CORRECTION

PATENT : 5,609,857

DATED : March 11, 1997

INVENTOR(S) : Rama S. Chandran, et al

It is certified that error appears in the above-identified patent and that said Letters Patent is hereby corrected as shown below:

Column 2, line 51, "moleties" should read --moieties--.

Column 2, line 52, "amine-containing moleties. Suitable moleties containing a" should read --amine-containing moieties. Suitable moieties containing a--.

Column 2, line 57, "moleties" should read --moieties--.

Column 3, line 7, "moleties" should read --moieties--.

Column 3, line 9, "moleties" should read --moieties--.

Column 8, line 61, "sulfate" should read --sulfate,--.

Signed and Sealed this

Seventeenth Day of March, 1998

BRUCE LEHMAN

*Attest:*

*Attesting Officer*     *Commissioner of Patents and Trademarks*